United States Patent [19]

Bachman et al.

[11] 4,194,051
[45] Mar. 18, 1980

[54] ASYMMETRIC CATALYSIS

[75] Inventors: Gerald L. Bachman; Billy D. Vineyard, both of St. Louis, Mo.

[73] Assignee: Monsanto Company, St. Louis, Mo.

[21] Appl. No.: 825,339

[22] Filed: Aug. 17, 1977

Related U.S. Application Data

[63] Continuation-in-part of Ser. No. 704,858, Jul. 14, 1976, which is a continuation of Ser. No. 607,090, Aug. 24, 1975, abandoned.

[51] Int. Cl.$^2$ .............................................. C07C 69/76
[52] U.S. Cl. ...................................... 560/60; 560/152; 560/170; 560/185; 562/470; 562/579
[58] Field of Search ................ 560/60, 170, 185, 152; 562/470, 579

[56] References Cited

FOREIGN PATENT DOCUMENTS 2123063 12/1971 Fed. Rep. of Germany .
2161200 6/1972 Fed. Rep. of Germany .

OTHER PUBLICATIONS

House, H. O., Modern Synthetic Reactions, pp. 28–34, 1972.

*Primary Examiner*—Paul J. Killos
*Attorney, Agent, or Firm*—Robert E. Wexler

[57] ABSTRACT

Catalytic asymmetric hydrogenation of a compound of the formula

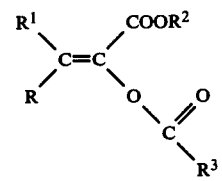

wherein R, $R^1$ and $R^2$ each independently represent hydrogen, substituted or unsubstituted alkyl having from 1 to 5 carbon atoms or substituted or unsubstituted aryl, and $R^3$ represents substituted or unsubstituted alkyl having from 1 to 5 carbon atoms or substituted or unsubstituted aryl, provided that, if only one of R and $R^1$ is hydrogen the Z geometric isomer is hydrogenated, in the presence of a homogeneous, coordination complex catalyst comprising rhodium, iridium or ruthenium in combination with an optically active bis phosphine ligand provides an excellent level of optical purity.

34 Claims, No Drawings

ASYMMETRIC CATALYSIS

CROSS REFERENCE TO RELATED APPLICATIONS

This is a continuation-in-part of copending application Ser. No. 704,858 filed July 14, 1976 which is a continuation of application Ser. No. 607,090 filed Aug. 24, 1975, now abandoned.

BACKGROUND OF THE INVENTION

This invention relates to new catalytic asymmetric hydrogenation processes. More specifically, this invention is directed to a hydrogenation process which provides excellent levels of optical purity.

Homogeneous catalysis, i.e., those catalyzed reactions that are conducted where both reactants and catalysts are soluble in the reaction mass, have been found to be particularly useful in processes wherein an asymmetric result is obtained. For instance, it has been found that when an olefin, which is capable of forming a racemic mixture is hydrogenated in the presence of a homogeneous, optically active catalyst, one or the other of the possible optical enantiomorphs is obtained in a major amount with the other optical enantiomorph being obtained in minor amounts. Furthermore, it has been found that certain such olefinic substrates, for instance, precursors of α-amino acids containing α-acrylamido substituents, are particularly amenable to hydrogenation with homogeneous, optically active catalysts. Such catalytic asymmetric hydrogenation processes have resulted in the production of large amounts of the desired optical enantiomorph. It has more recently been found that certain homogeneous, optically active catalysts containing optically active bis phosphine ligands provide excellent levels of optical purity, reaching 80% and higher with such α-amino acid precursors. Other olefinic substrates which would provide excellent levels of optical purity, upon hydrogenation, are particularly desirable.

It is an object of the present invention to provide such olefinic substrates.

It is a further object to provide novel catalytic asymmetric hydrogenation processes which produce large amounts of the desired optical enantiomorph.

These and other objects, aspects and advantages of this invention will become apparent from a consideration of the accompanying specification and claims.

SUMMARY OF THE INVENTION

In accordance with the above objects, the present invention provides catalytic hydrogenation of a compound of the formula

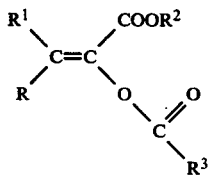

wherein R, $R^1$ and $R^2$ each independently represent hydrogen, substituted or unsubstituted alkyl having from 1 to 5 carbon atoms or substituted or unsubstituted aryl, and $R^3$ represents substituted or unsubstituted alkyl having from 1 to 5 carbon atoms or substituted or unsubstituted aryl, provided that, if only one of R and $R^1$ is hydrogen the Z geometric isomer is hydrogenated, in the presence of a homogeneous, coordination complex catalyst comprising rhodium, iridium or ruthenium in combination with an optically active bis phosphine ligand. This process provides excellent levels of optical purity of desired optical enantiomorphs.

DESCRIPTION OF THE PREFERRED EMBODIMENTS

The hydrogenation reaction is illustrated by the following equation:

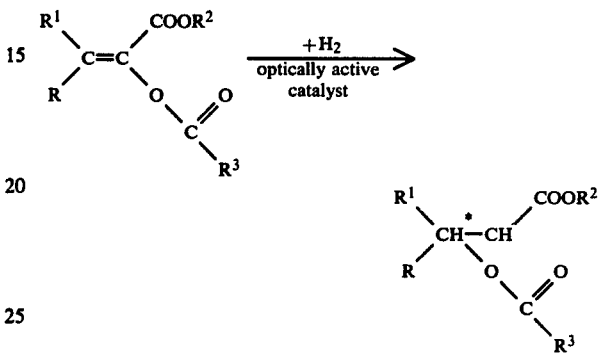

*shows one or both carbon atoms are asymmetric wherein R, $R^1$, $R^2$ and $R^3$ have the same meaning as described above.

It has been found that if one of R and $R^1$ is hydrogen, the geometric stereochemistry of the olefinic substrate being hydrogenated effects the results obtained. In general, if one of R and $R^1$ is hydrogen, it is necessary to utilize the Z geometric isomer of the compound to realize the excellent levels of optical purity with the process of this invention. Those skilled in the art will recognize that E and Z geometric isomers exist only when R and $R^1$ are different, and therefore said isomers do not exist when R and $R^1$ are both hydrogen. In the case of R and $R^1$ both being hydrogen, excellent results have been achieved with the process of this invention. The E and Z geometric isomer nomenclature is described in detail in The Journal of Organic Chemistry, Vol. 35, No. 9, September 1970, pp. 2849-67.

R, $R^1$, $R^2$ and $R^3$ can be exemplified by alkyl groups such as methyl, ethyl, propyl, etc., and by aryl groups such as phenyl, 4-chlorophenyl, 3,4-dihydroxyphenyl, 4-methylphenyl, etc. Those skilled in the art will recognize that such substituents can be selected from a large number of groups and that this is limited only by the optical enantiomorph that is the desired end-product. Furthermore, it may occur that such substituent groups are themselves precursors of substituents that are desired substituents. For instance, if the desired substituent was hydroxyl the unsaturated precursor might contain the substituent

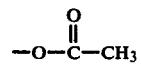

which would provide the hydroxyl by simple hydrolysis after the catalytic asymmetric hydrogenation.

The optical enantiomorphs resulting from the process of this invention are particularly desirable in that optical activity is a characteristic of compounds which are biologically active, i.e., normally only one or the other optical enantiomorphs is useful in living organisms. For instance, those optical enantiomorphs resulting from this process which have an α-hydroxy (resulting from simple hydrolysis) substituent on a carboxylic acid are recognized as replacements for α-amino acids.

It has surprisingly been found that compounds within the general structural formula described herein for the olefinic substrate provide excellent results with the process of this invention. Optical purity levels of about 65% to about 95%, determined by the following equation, are obtained with this invention (it being understood that the optical activity, expressed as specific rotation, is measured in the same solvent);

% Optical Purity = $\dfrac{\text{Observed optical activity of the mixture} \times 100}{\text{Optical activity of pure optical isomer}}$ The following are exemplary compounds useful as olefinic substrates in the hydrogenation process of this invention. It is recognized that, an previously mentioned, it is necessary in the case of some of these compounds to utilize a particular geometric isomer of the compound:

ethyl 2-acetyloxy-3-(p-chlorophenyl)-2-propenoate
propyl 2-propyloxy-3-phenyl-2-propenoate
ethyl 2-propyloxy-3-phenyl-2-propenoate
ethyl 2-acetyloxy-3-(p-methylphenyl)-2-propenoate
methyl 2-acetyloxy-3-(o-methylphenyl)-2-propenoate
propyl 2-acetyloxy-3-phenyl-2-propenoate
ethyl 2-butyloxy-3-phenyl-2-propenoate
phenyl 2-butyloxy-3-phenyl-2-propenoate
ethyl 2-acetyloxy-2-butenoate
ethyl 2-acetyloxy-2-pentenoate
ethyl 2-butyloxy-2-propenoate
methyl 2-butyloxy-2-propenoate
propyl 2-acetyloxy-2-propenoate
phenyl 2-acetyloxy-2-propenoate
ethyl 2-propyloxy-2-propenoate
ethyl 2-acetyloxy-3-(3'-indolyl)-2-propenoate
ethyl 2-acetyloxy-4-methyl-2-pentenoate
ethyl 2-acetyloxy-6-acetylamino-2-hexenoate
methyl 2-acetyloxy-4-methylthio-2-butenoate
methyl 2-acetyloxy-3-(3'-indolyl)-2-propenoate
methyl 2-acetyloxy-3,3-dimethyl-2-propenoate
ethyl 2-acetyloxy-3-methyl-2-pentenoate
phenyl 2-acetyloxy-3-methyl-2-pentenoate A preferred embodiment of this invention is the catalytic asymmetric hydrogenation of the Z isomers of compounds represented by the formula provided above. Another preferred embodiment is the catalytic asymmetric hydrogenation of compounds of said formula wherein R and $R^1$ are the same.

A particularly preferred embodiment of this invention is the asymmetric hydrogenation of compounds represented by the formula:

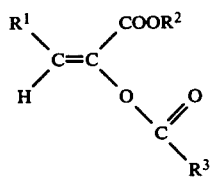

provided that, if $R^1$ is not hydrogen the Z geometric isomer is hydrogenated, wherein $R^1$, $R^2$ and $R^3$ have the same meaning as described above. For these preferred embodiments, optical purity levels exceeding 80 percent, determined as previously described, are achievable with the process of this invention.

Still more particularly preferred embodiments of this invention are the catalytic asymmmetric hydrogenation of (Z)-ethyl 2-acetyloxy-3-phenyl-2-propenoate, (Z)-methyl 2-acetyloxy-3-phenyl-2-propenoate, methyl 2-acetyloxy-2-propenoate and ethyl 2-acetyloxy-2-propenoate. For these preferred embodiments optical purity levels exceeding 80 percent, determined as previously described, are achievable with the process of this invention.

The D or L enantiomorphs of phenyllactic acid and lactic acid can be readily obtained by such procedures.

Such hydrogenation reactions are usually conducted in a solvent, such as benzene, methanol, ethanol, 2-propanol, toluene, cyclohexane, and mixtures of these solvents. Almost any aromatic or saturated alkane or cycloalkane solvent, which is inactive to the hydrogenation conditions of this reaction, can be used. The preferred solvents are alcohols particularly methanol, ethanol and 2-propanol. More particularly preferred are those alcohols corresponding to the ester group in the olefinic substrate being hydrogenated.

The homogeneous, optically active catalysts useful in this invention are soluble coordination complexes comprising a metal which is rhodium, iridium or ruthenium in combination with at least one optically active bis phosphine ligand, preferably at least about 0.5 moles of bis phosphine ligand per mole of metal. These catalysts are soluble in the reaction mass and are therefore referred to as "homogeneous" catalysts.

These catalysts contain optically active bis phosphine compounds of general formulae I and II below. These bis phosphine compounds are characterized by the structural formula

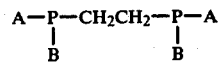

wherein A and B each independently represent substituted or unsubstituted alkyl of from 1 to 12 carbon atoms, substituted or unsubstituted cycloalkyl having from 4 to 7 carbon atoms, or substituted or unsubstituted aryl; provided that such substituents provide no significant interference with the steric requirements around the phosphorous atom and A and B are different.

Among such bis phosphine compounds, those having two dissimilar aryl groups on each phosphorus atom are also preferred, particularly those wherein one such aryl group has an alkoxy substituent at the ortho position.

More preferred bis phosphine compounds useful in the present invention are the optically active bis phosphines characterized by the structural formula

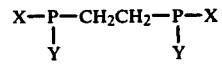

wherein
X represents substituted or unsubstituted phenyl,
Y represents substituted or unsubstituted 2-alkoxyphenyl wherein the alkoxy has from 1 to 6 carbon atoms; provided that such substituents provide no significant interference with the steric requirements around the phosphorus atom and X and Y are different.

Still more particularly preferred optically active bis phosphine compounds useful in the present invention are characterized by the structural formula

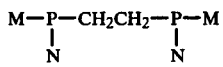 III wherein
M represents

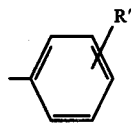,

N represents

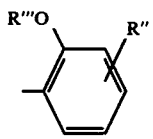,

R' and R" each independently represent hydrogen, halogen, alkyl having from 1 to 6 carbon atoms or alkoxy having from 1 to 6 carbon atoms, and
R''' represents alkyl having from 1 to 6 carbon atoms; provided that M and N are different.

A particularly preferred optically active bis phosphine compound useful in the present invention is 1,2-bis(o-anisylphenylphosphino)ethane.

Other exemplary optically active bis phosphine compounds useful in this invention are:

1,2-bis(o-anisyl-4-methylphenylphosphino)ethane
1,2-bis(o-anisyl-4-chlorophenylphosphino)ethane
1,2-bis(o-anisyl-3-chlorophenylphosphino)ethane
1,2-bis(o-anisyl-4-bromophenylphosphino)ethane
1,2-bis[(2-methoxy-5-chlorophenyl)-phenylphosphino]ethane
1,2-bis[(2-methoxy-5-bromophenyl)-phenylphosphino]ethane
1,2-bis(2-ethoxyphenylphenylphosphino)ethane
1,2-bis[o-anisyl-(p-phenylphenyl) phosphino]ethane
1,2-bis[(2-methoxy-4-methylphenyl)-phenylphosphino]ethane
1,2-bis(2-ethoxyphenyl-4-chlorophenylphosphino)ethane
1,2-bis(o-anisyl-2-methylphenylphosphino)ethane
1,2-bis(o-anisyl-4-ethylphenylphosphino)ethane
1,2-bis(o-anisyl-3-ethylphenylphosphino)ethane
1,2-bis(o-anisyl-3-phenylphenylphosphino)ethane For these bis phosphine compounds to be useful in asymmetric hydrogenation reactions they must be utilized as the optically active enantiomorph and not in the meso form.

Optical activity of the coordinated complex catalysts useful in this invention resides in the bis phosphine ligand. This optical activity results from having two different groups, in addition to the ethane bridge, on the phosphorus atom.

Illustrative coordination metal complexes can be represented by the formula MeTL wherein Me is a transition metal selected from the group consisting of rhodium, iridium and ruthenium; T is selected from the group consisting of hydrogen, fluroine, bromine, chlorine and iodine; L is the optically active bis phosphine ligand as previously defined.

It has been found that excellent levels of optical purity of the desired optical enantiomorphs can be achieved not only with the above-described catalysts represented by the formula MeTL, which are coordination complexes of a metal selected from the group consisting of rhodium, iridium and ruthenium, but can also be achieved when the hydrogenation is carried out in the presence of an in situ complex catalyst that comprises a solution of a transition metal selected from the group consisting of rhodium, iridium and ruthenium and at least about 0.5 moles of the optically active bis phosphine ligand per mole of metal. For instance, such catalysts can be prepared by dissolving a soluble compound of the appropriate metal in a suitable solvent together with an optically active bis phosphine compound as the ligand wherein the ratio of ligand to metal is at least 0.5 moles of ligand per mole of metal, preferably one mole of ligand per mole of metal. It has been found that the catalyst is formed in situ by adding a soluble metal compound to the reaction mass together with the addition of the proper amount of the optically active bis phosphine ligand to the reaction mass either before or during hydrogenation.

The preferred metal for use in this process is rhodium. Soluble rhodium compounds that can be utilized include rhodium trichloride hydrate, rhodium tribromide hydrate, rhodium sulfate, organic rhodium complexes with ethylene, propylene, etc., and bis olefins such as 1,5-cyclooctadiene and 1,5-hexadiene, bicyclo-2.2.1-hepta-2,5-diene and other dienes which can form bidentate ligands, or an active form of metallic rhodium that is readily solubilized.

It has been found that a preferred embodiment of this invention is the hydrogenation process where the optically active bis phosphine ligand is present in a ratio of about 0.5 to about 2.0, preferably 1.0, moles of bis phosphine ligand per mole of metal. In practice, it is preferred to have the optically active catalyst in a solid form for purposes of handling and storage. It has been found that excellent results can be obtained with solid, cationic coordination metal complexes.

Cationic coordination metal complexes containing one mole of the optically active bis phosphine ligand per mole of metal and a chelating bis olefin represent a preferred form of the catalysts useful in the present invention. For instance, using organic rhodium complexes, as described above, one can prepare such cationic coordination rhodium complexes by slurrying the organic rhodium complex in an alcohol, such as ethanol, adding one mole per mole of rhodium of the optically active bis phosphine compound so that an ionic solution is formed, followed by the addition of a suitable anion, such as, for instance, tetrafluoroborate, tetraphenylborate or any other anion that will result in the precipitation or crystallization of a solid, cationic coordination metal complex either directly from the solvent or upon treatment in an appropriate solvent.

Exemplary cationic coordination metal complexes are cyclooctadiene-1,5-[1,2-bis(o-anisylphenylphosphino)ethane] rhodium tetrafluoroborate, cyclooctadiene-1,5-[1,2-bis(o-anisylphenylphosphino)ethane] rhodium tetraphenyl borate and bicycio-2.2.1-hepta-2,5-diene-[1,2-bis(o-anisylphenylphosphino)ethane] rhodium tetrafluoroborate.

Without prejudice to the present invention it is thought that the catalyst is present actually as a catalyst precursor and that upon contact with hydrogen the catalyst is converted to an active form. This conversion can, of course, be carried out during the actual hydrogenation or can be accomplished by subjecting the catalyst (or precursor) to hydrogen prior to addition to the reaction mass to be hydrogenated.

As previously noted, the catalyst can be added to the solvent either as a compound per se or as its components which then form the catalyst in situ. When the catalyst is added as its components it may be added prior to or after the addition of the olefinic substrate. Components for the preparation of the catalyst in situ are the soluble metal compound and the optically active bis phosphine compound. The catalyst can be added in any effective catalytic amount and generally in the range of about 0.001 percent to about 5 percent by weight of contained metal based on the olefinic substrate to by hydrogenated.

Within the practical limits, means should be provided so as to avoid contacting the catalyst or reaction mass with oxidizing materials. In particular, care should be taken so as to avoid contact with oxygen. It is preferred to carry out the hydrogenation reaction preparation and actual reaction in gases (other than $H_2$) that are inert to both reactants and catalysts such as, for instance, nitrogen or argon.

After addition of the reactants and catalyst to the solvent, hydrogen is added to the mixture until about 0.5 to about 5 times the mole quantity of the olefinic substrate present has been added. The pressure of the system will necessarily vary since it will be dependent upon the type of reactant, type of catalyst, size of hydrogenation apparatus, amount of reactants and catalyst and amount of solvent. Lower pressures, including atmospheric and sub-atmospheric pressure can be used as well as higher pressure.

Reaction temperatures may be in the range of about $-20°$ C. to about $110°$ C. Higher temperatures may be used but are normally not required and may lead to an increase of side reactions.

Upon completion of the reaction, which is determined by conventional means, the product is recovered by conventional means.

Many naturally occurring products and medicaments exist in an optically active form. In these cases only the L or D form is usually effective. Synthetic preparation of these compounds in the past has required an additional step of separating the product into its enantiomorphs. This process is expensive and time-consuming. The process of the present invention permits the direct formation of desired optical enantiomorphs with excellent optical purity thus eliminating much of the time-consuming and expensive separation of such optical enantiomorphs. Furthermore, the process provides a higher yield of the desired optical enantiomorph while concurrently decreasing the yield of the unwanted optical enantiomorph.

The hydrogenation process of this invention is particularly desirable because of its ability to not only provide an unusually high optical purity of the desired optical enantiomorph but also because of its ability to afford a rapid rate of hydrogenation at low catalyst concentrations.

The following examples will serve to illustrate certain specific embodiments within the scope of this invention and are not to be construed as limiting the scope thereof. In the examples, the percent optical purity is determined by the equation previously set forth.

EXAMPLE I

Preparation of (Z)-ethyl 2-acetyloxy-3-phenyl-2-propenoate

A solution containing 22 g. of ethyl phenylpyruvate, 65 g. of acetic anhydride and 20 mg. of p-toluenesulfonic acid monohydrate was refluxed for 2.5 hours. Excess acetic anhydride was stripped from the reaction mass and the product, crude (Z)-ethyl 2-acetyloxy-3-phenyl-2-propenoate, was distilled at about 1.6 mm. Hg. (b.p. 120°–135° C.). The recovered product crystallized on standing in refrigeration and was recovered by filtration and recrystallized from ethanol; recovered 12.1 g., m.p. 41°–47° C.; second recrystallization, 10.5 g., m.p. 47°–49° C.; third recrystallization, 9.2 g., m.p., 47°–49° C.

EXAMPLE II

Hydrogenation of (Z)-ethyl 2-acetyloxy-3-phenyl-2-propenoate (A) 1.9903 g. of (Z)-ethyl 2-acetyloxy-3-phenyl-2-propenoate and 0.0175 g. of cyclooctadiene-1,5-[1,2-bis-(o-anisylphenylphosphino)ethane] rhodium tetrafluoroborate in 30 cc. of ethanol was shaken in a Hoke bomb at about 27 atm. (abs.) and 50° C. Hydrogen uptake was essentially complete in 2 hours. The resulting solution was sripped of ethanol on a rotary evaporator and examined by NMR which confirmed the presence of the hydrogenation product, ethyl 2-acetyloxy-3-phenyl-propanoate, as an oil. The product was recovered by vacuum distillation. 1.6 g. of distillate, b.p. 80°–83° C. at 0.05 mm. Hg. were recovered. NMR assay shows the product to consist of 97.6% of the desired hydrogenation product and 2.4% of the starting olefin. Gas chromatography confirmed this assay. The $[\alpha]_D^{20} = -6.91°$ (C=6.0 in $CHCl_3$). Optical purity was 79.4 percent, if adjusted for assay would be 81.5 percent [pure $[\alpha]_D^{23} = -8.7°$ (C=6.65 in $CHCl_3$), J. Am. Chem. Soc. 86, 5326 (1964)].

(B) 2.2721 g. of (Z)-ethyl 2-acetyloxy-3-phenyl-2-propenoate and 0.0202 g. cyclooctadiene-1,5-[1,2-bis(o-anisylphenylphosphino)ethane] rhodium tetrafluoroborate in 30 cc. of ethanol was subjected to 3 atm. (abs.) $H_2$ pressure at 51° C. The resulting solution was stripped of ethanol on a rotary evaporator. NMR shows 89 percent completion after 6 hours. The product, ethyl 2-acetyloxy-3-phenylpropanoate, was recovered by flash distillation, b.p. 80°–85° C. at 0.5 mm. Hg. NMR assay shows 87.0 percent of the desired product. The observed rotation of the product was $-0.515°$ which converts to $[\alpha]_D^{20} = 8.27°$ (C=6.0 in $CHCl_3$). Optical purity adjusted for assay was 95 percent.

EXAMPLE III

Hydrogenation of ethyl 2-acetyloxy-2-propenoate

A solution of 2.0156 g. of ethyl 2- acetyloxy -2-propenoate (in 0.2% hydroquinone) and 0.0187 g. of cyclooctadiene-1,5[1,2-bis(o-anisylphenylphosphino)ethane] rhodium tetrafluoroborate in 25 ml. of ethanol was hydrogenated at 50° C. and 2.5 to 3.2 atm. (abs.) $H_2$ pressure. Hydrogen uptake was complete in 24 minutes. The resulting solution was stripped of ethanol at 40° C. and 20 mm. Hg. pressure. Approximately 0.3 g. was lost during the stripping leaving approximately 1.7 g. of crude product. The crude product was vacuum distilled and yielded 1.5 g. of product, b.p. about 80° C. at 17 mm. Hg. The pot residue was not distilled to complete dryness. NMR indicated essentially complete conversion to the hydrogenation product. The $[\alpha]_D^{20} = -44.8°$ (C=1 in CHCl$_3$). The optical purity was 94.1 percent [pure $[\alpha]_D^{22} = -47.6°$ (C=0.9 in CHCl$_3$), J. Am. Chem. Soc. 85, 1685 (1963)].

The above Examples II and III demonstrate the excellent results achievable by the process of this invention. By way of comparison, Examples IV–VIII, following, illustrate the inferior results obtained with substrates outside the scope of this invention.

EXAMPLE IV

Hydrogenation of mixture of (E) and (Z)-ethyl 2-acetyloxy-3-phenyl-2-propenoate

A solution of 0.5358 g. of ethyl 2-acetyloxy-3-phenyl-2-propenoate, Z/E=52:48, and 0.0054 g. of cyclooctadiene-1,5[1,2-bis(o-anisylphenylphosphino)ethane] rhodium tetrafluoroborate in 10 ml. of ethanol was hydrogenated at 50° C. and 4.4 atm. (abs.) of hydrogen pressure for 7 hours. NMR indicated that the mixture was at least 95 percent hydrogenated. The $[\alpha]_D^{20} = -5.4°$ (C=1 in ethanol).

Under substantially the same conditions the Z isomer alone was hydrogenated. A solution of 1.0204 g. of (Z)-ethyl 2-acetyloxy-3-phenyl-2-propenoate and 0.0109 g. of cyclooctadiene-1,5[1,2-bis(o-anisylphenylphosphino)ethane] rhodium tetrafluoroborate in 25 ml. of ethanol was hydrogenated at 50° C. and 3.7 atm. (abs.) of hydrogen pressure. Hydrogen uptake was essentially complete in 2.5 hours. The solution was held at reaction conditions for a total of 6 hours. The solution was diluted to 100 ml. with ethanol and examination by polarimeter indicated $[\alpha]_D^{20} = -10°$ (C=1 in ethanol).

Comparing the $[\alpha]_D^{20}$ obtained for the hydrogenated Z/E mixture with the $[\alpha]_D^{20}$ obtained for the Z isomer hydrogenated alone, it is concluded that the optical purity resulting from the hydrogenation of the E isomer was less than 10 percent.

EXAMPLE V

Preparation of (Z)-ethyl 3-acetyloxy-3-phenyl-2-propenoate

A solution of 27.8 g. (0.145 mole) of ethyl 3-oxo-3-phenylpropanoate, 29.0 g. of 2-acetyloxy-1-propene, and 100 mg. of p-toluenesulfonic acid monohydrate was heated to reflux for 17 hours. The reaction mass was poured into 50 ml. of a 5° C. saturated solution of NaHCO$_3$ and the organic phase was extracted into ethyl ether. The ether solution was dried and the solvent was stripped off. Distillation of the residue at 0.1 mm. of Hg. yielded 8.3 g. of a yellow oil, b.p. 110°–120° C. The distillate was shown by GLC, NMR and UV analysis to be (Z)-ethyl 3-acetyloxy-3-phenyl-2-propenoate.

EXAMPLE VI

Hydrogenation of (Z)-ethyl 3-acetyloxy-3-phenyl-2-propenoate

A solution of 2.65 g. of (Z)-ethyl 3-acetyloxy-3-phenyl-2-propenoate and 0.0373 g. of cyclooctadiene-1,5-[1,2-bis(o-anisylphenylphosphino)ethane] rhodium tetrafluoroborate in 30 cc. of ethanol was hydrogenated at 27 atm. (abs.) and 50° C. in a Hoke bomb. After 12 hours the product was isolated by removing the ethanol on a rotary evaporator. NMR analysis indicated that the hydrogenation product to olefin ratio was 89:11. In addition, some ethyl 3-phenylpropanoate was present, which arose from hydrogenolysis.

2.5 g. of crude product was subjected to distillation, a first fraction was collected, b.p. 75°–87° C. at 0.1 mm. of Hg., which was ethyl 3-phenylpropanoate. The remaining material that distilled at 95°–110° C. and 0.1 mm. of Hg. was an 86:14 (NMR) mixture of ethyl 3-acetyloxy-3-phenylpropanoate and (Z)-ethyl 3-acetyloxy-3-phenyl-2-propenoate.

The $[\alpha]_D^{20} = -4.74°$ (neat, L=1), which indicates an optical purity less than 10 percent.

EXAMPLE VII

Preparation of (E)-ethyl 3-acetyloxy-3-phenyl-2-propenoate

A solution of 5.2 g. of (Z)-ethyl 3-acetyloxy-3-phenyl-2-propenoate in 60 ml. of CHCl$_3$ was irradiated with 3100 Å light for 72 hours. The solvent was removed on a rotary evaporator. Distillation of the residue at 0.03 mm. of Hg. yielded 1.3 g. of yellow oil, b.p. 92°–98° C. The distillate was shown by GLC, NMR, and UV analysis to be (E)-ethyl 3-acetyloxy-3-phenyl-2-propenoate of 86 percent purity.

EXAMPLE VIII

Hydrogenation of (E)-ethyl 3-acetyloxy-3-phenyl-2-propenoate

A solution of 1.1566 g. of the (E)-ethyl 3-acetyloxy-3-phenyl-2-propenoate prepared in Example VII (86 percent purity) and 0.027 g. of cyclooctadiene-1,5-[1,2-bis-(o-anisylphenylphosphino)ethane] rhodium tetrafluoroborate in 30 cc. of ethanol was hydrogenated for 5 hours at 27 atm. (abs.) and 50° C. Ethanol was then stripped on a rotary evaporator and the product examined by NMR analysis. The hydrogenation product to olefin ratio was 76:24. This product mix was distilled at 95°–120° C. and 0.2 mm. of Hg. Gas chromatography assay of the distillate indicated the ethyl 3-acetyloxy-3-phenylpropanoate to (E)-ethyl 3-acetyloxy-3-phenyl-2-propenoate to ethyl 3-phenylpropanoate ratio was 64:18:18.

The product mixture had an $[\alpha]_D^{20} = +0.515°$ (neat, L=1), which corrected for assay gives $[\alpha]_D^{20} = +0.805°$ (neat, L=1). This represents an optical purity of less than 1 percent.

While the invention has been described herein with regard to certain specific embodiments, it is not so limited. It is to be understood that variations and modifications thereof may be made by those skilled in the art without departing from the spirit and scope of the invention.

The embodiments of this invention in which a particular property or privilege is claimed are defined as follows:

1. An asymmetric hydrogenation process affording an optical purity of enantiomorph of at least about 86 percent comprising hydrogenating a compound of the formula

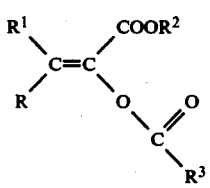

wherein R, $R^1$ and $R^2$ each independently represent hydrogen, substituted or unsubstituted alkyl having from 1 to 5 carbon atoms or substituted or unsubstituted aryl, and $R^3$ represents substituted or unsubstituted alkyl having from 1 to 5 carbon atoms or substituted or unsubstituted aryl, provided that, if only one of R and $R^1$ is hydrogen the Z geometric isomer is hydrogenated, in the presence of from about 0.001% to about 5% by weight, based on said compound, of a homogeneous, coordination complex of rhodium, iridium or ruthenium in combination with an optically active bis phosphine ligand represented by the formula

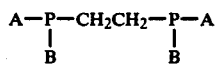

wherein A and B each independently represent substituted or unsubstituted alkyl of from 1 to 12 carbon atoms, substituted or unsubstituted cyclo alkyl having from 4 to 7 carbon atoms, or substituted or unsubstituted aryl; provided that such substituents provide no significant interference with the steric requirements around the phosphorus atom and A and B are different, said process being conducted at a temperature of from about $-20°$ C. to about $110°$ C. and said hydrogen concentration being equal to about 0.5 to about 5 times the mole quantity of said compound.

2. A process according to claim 1 wherein the bis phosphine ligand is represented by the formula

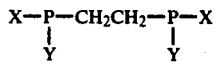

wherein
X represents substituted or unsubstituted phenyl,
Y represents substituted or unsubstituted 2-alkoxyphenyl wherein the alkoxy has from 1 to 6 carbon atoms; provided that such substituents provide no significant interference with the steric requirements around the phosphorus atom and X and Y are different.

3. A process according to claim 1 wherein the bis phosphine ligand is represented by the formula

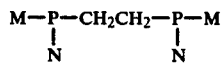

wherein
M represents

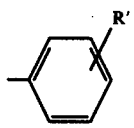

N represents

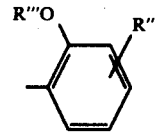

R' and R" each independently represent hydrogen, halogen, alkyl having from 1 to 6 carbon atoms or alkoxy having from 1 to 6 carbon atoms, and
R''' represents alkyl having from 1 to 6 carbon atoms; provided that M and N are different.

4. A process according to claim 1 wherein the bis phosphine ligand is 1,2-bis(o-anisylphenylphosphino)ethane.

5. A process according to claim 1 wherein the metal utilized in the catalyst complex is rhodium.

6. A process according to claim 2 wherein the metal utilized in the catalyst complex is rhodium.

7. A process according to claim 3 wherein the metal utilized in the catalyst complex is rhodium.

8. A process according to claim 4 wherein the metal utilized in the catalyst complex is rhodium.

9. A process according to claim 1 wherein the compound being hydrogenated is represented by the formula

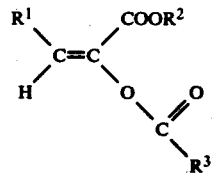

provided that, if $R^1$ is not hydrogen the Z geometric isomer is hydrogenated.

10. A process according to claim 2 wherein the compound being hydrogenated is represented by the formula

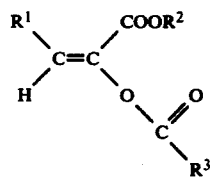

provided that, if $R^1$ is not hydrogen the Z geometric isomer is hydrogenated.

11. A process according to claim 3 wherein the compound being hydrogenated is represented by the formula

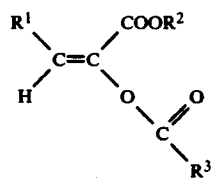

provided that, if $R^1$ is not hydrogen the Z geometric isomer is hydrogenated.

12. A process according to claim 4 wherein the compound being hydrogenated is represented by the formula

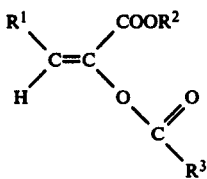

provided that, if $R^1$ is not hydrogen the Z geometric isomer is hydrogenated.

13. A process according to claim 5 wherein the compound being hydrogenated is represented by the formula

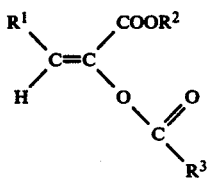

provided that, if $R^1$ is not hydrogen the Z geometric isomer is hydrogenated.

14. A process according to claim 6 wherein the compound being hydrogenated is represented by the formula

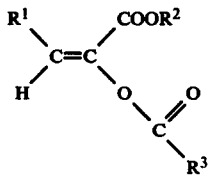

provided that, if $R^1$ is not hydrogen the Z geometric isomer is hydrogenated.

15. A process according to claim 7 wherein the compound being hydrogenated is represented by the formula

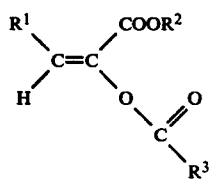

provided that, if $R^1$ is not hydrogen the Z geometric isomer is hydrogenated.

16. A process according to claim 8 wherein the compound being hydrogenated is represented by the formula

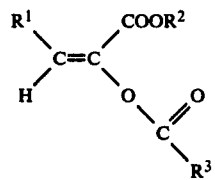

provided that, if $R^1$ is not hydrogen the Z geometric isomer is hydrogenated.

17. A process according to claim 9 wherein the compound being hydrogenated is (Z)-ethyl 2-acetyloxy-3-phenyl-2-propenoate.

18. A process according to claim 9 wherein the compound being hydrogenated is ethyl 2-acetyloxy-2-propenoate.

19. A process according to claim 10 wherein the compound being hydrogenated is (Z)-ethyl 2-acetyloxy-3-phenyl-2-propenoate.

20. A process according to claim 10 wherein the compound being hydrogenated is ethyl 2-acetyloxy-2-propenoate.

21. A process according to claim 11 wherein the compound being hydrogenated is (Z)-ethyl 2-acetyloxy-3-phenyl-2-propenoate.

22. A process according to claim 11 wherein the compound being hydrogenated is ethyl 2-acetyloxy-2-propenoate.

23. A process according to claim 12 wherein the compound being hydrogenated is (Z)-ethyl 2-acetyloxy-3-phenyl-2-propenoate.

24. A process according to claim 12 wherein the compound being hydrogenated is ethyl 2-acetyloxy-2-propenoate.

25. A process according to claim 13 wherein the compound being hydrogenated is (Z)-ethyl 2-acetyloxy-3-phenyl-2-propenoate.

26. A process according to claim 13 wherein the compound being hydrogenated is ethyl 2-acetyloxy-2-propenoate.

27. A process according to claim 14 wherein the compound being hydrogenated is (Z)-ethyl 2-acetyloxy-3-phenyl-2-propenoate.

28. A process according to claim 14 wherein the compound being hydrogenated is ethyl 2-acetyloxy-2-propenoate.

29. A process according to claim 15 wherein the compound being hydrogenated is (Z)-ethyl 2-acetyloxy-3-phenyl-2-propenoate.

30. A process according to claim 15 wherein the compound being hydrogenated is ethyl 2-acetyloxy-2-propenoate.

31. A process according to claim 16 wherein the compound being hydrogenated is (Z)-ethyl 2-acetyloxy-3-phenyl-2-propenoate.

32. A process according to claim 16 wherein the compound being hydrogenated is ethyl 2-acetyloxy-2-propenoate.

33. A process according to claim 1 wherein the Z geometric isomer of the compound is hydrogenated if said compound exists as a Z and E geometric isomer.

34. A process according to claim 1 wherein R and $R^1$ are the same.

* * * * *

UNITED STATES PATENT AND TRADEMARK OFFICE
CERTIFICATE OF CORRECTION

PATENT NO. : 4,194,051
DATED : March 18, 1980
INVENTOR(S) : GERALD L. BACHMAN AND BILLY D. VINEYARD It is certified that error appears in the above-identified patent and that said Letters Patent are hereby corrected as shown below:

Column 1, line 29, "acrylamido" should read -- acylamido --.

Column 4, line 4, "asymmmetric" should read -- asymmetric --.

Column 7, line 20, "by" should read -- be --.

Signed and Sealed this

First Day of July 1980

[SEAL]

Attest:

SIDNEY A. DIAMOND

Attesting Officer     Commissioner of Patents and Trademarks